United States Patent
Prasad et al.

Patent Number: 5,543,543
Date of Patent: Aug. 6, 1996

[54] PROCESS FOR PREPARING PHOSPHORODICHLORIDODITHIOATES BY REACTING ALKYL MERCAPTANS WITH PCl₃, PSCl₃ AND SULFUR

[75] Inventors: Vidyanatha A. Prasad; Peter E. Newallis, both of Leawood, Kans.; Emerson L. Foote, Jr., Kansas City, Mo.

[73] Assignee: Bayer Corporation, Pittsburgh, Pa.

[21] Appl. No.: 442,623

[22] Filed: May 17, 1995

[51] Int. Cl.⁶ ..................................................... C07F 9/20
[52] U.S. Cl. .................................................... 558/96
[58] Field of Search ............................................. 558/96

[56] References Cited

U.S. PATENT DOCUMENTS

| | | | |
|---|---|---|---|
| 3,879,500 | 4/1975 | Uhing et al. | 260/981 |
| 4,035,449 | 7/1977 | Zakaryan | 558/97 |
| 4,082,822 | 4/1978 | Diehr et al. | 260/972 |
| 4,120,917 | 10/1978 | Schmitt | 558/96 |
| 4,251,469 | 2/1981 | Zinke et al. | 558/96 X |
| 5,081,272 | 1/1992 | Wehrenberg | 558/90 |

FOREIGN PATENT DOCUMENTS 187785 10/1966 U.S.S.R. .

OTHER PUBLICATIONS

Houben–Weyl: "Die Methoden der Organischen Chemie" (The Methods of Organic Chemistry) vol. 12/2, p. 682 (Month unavailable) 1994, Gerorge Thieme Verlag Stuttgart.

*Primary Examiner*—Johann Richter
*Assistant Examiner*—Michael G. Ambrose
*Attorney, Agent, or Firm*—Joseph C. Gil; Godfried R. Akorli

[57] ABSTRACT

Disclosed herein is a process for preparing a phosphorodichloridodithioate comprising reacting a mercaptan, phosphorus trichloride, thiophosphoryl chloride and sulfur in the presence of a base catalyst.

9 Claims, No Drawings

PROCESS FOR PREPARING PHOSPHORODICHLORIDODITHIOATES BY REACTING ALKYL MERCAPTANS WITH PCl₃ PSCl₃ AND SULFUR

BACKGROUND OF THE INVENTION

1. Field of the Invention

The present invention relates to an improved process for the preparation of phosphorodichloridodithioates that can be used as intermediates for the synthesis of insecticidally active compounds.

2. Brief Description of the Prior Art

Disclosed by the prior art is a process for preparing phosphorodichloridodithioates by heating the corresponding phosphoric acid alkyl ester dichlorides with phosphorus(V) sulfide to 140°–150° C. (see Houben-Weyl: "Die Methoden der Organischen Chemie" (The Methods of Organic Chemistry), Volume 12/2, page 682 [1964], George Thieme Verlag Stuttgart). Alternately, O-alkyl ester dichlorides can be reacted directly with phosphorus(V) sulfide to give the dithiophosphoric acid alkyl ester dichlorides.

In carrying out these processes industrially, one finds problems in separating and removing the phosphorus pentoxide by-product. After separating the resulting dithiophosphoric acid alkyl ester dichlorides, there remain solid phosphorus pentoxide and sulphur-containing, extremely malodorous compounds. Their removal to leave an odor-free product, say by oxidation in an alkaline medium, is only partially feasible, and requires long times and high costs.

Another method of preparing phosphorodichloridodithioates comprises reacting elemental sulfur with thiophosphoric acid ester dichlorides that are obtained from the reaction of thiols and phosphorus trichloride. The reaction of sulfur with the thiophosphoric acid ester dichlorides only takes place at temperatures above 100° C. Sulfurization the thiophosphoric acid ester dichlorides is attended by a marked disproportionation to dithiophosphoric acid diester chlorides and phosphorus trichloride. To suppress the disproportionation, the sulfurization must be carried out under pressure (see Houben-Weyl, loc. cit.).

U.S. Pat. No. 3,879,500 and Russian Patent No. 187,785 disclose what appears to be a simple method of preparing phosphorodichloridodithioates. The method comprises reacting corresponding thiol compounds with thiophosphoryl chloride. However, if too large an amount of the thiol compound is employed in this reaction, trithiophosphoric acid diester chlorides and tetrathiophosphoric acid esters are obtained, almost exclusively as the reaction product even in the presence of acid-binding agents (see also Houben-Weyl, loc. cit.).

U.S. Pat. No. 4,082,822 discloses a process for the preparation of a phosphorodichloridodithioate by reacting a thiol compound with a thiophosphoryl halide in the presence of a catalyst. Distinctly, the catalyst is selected from the group consisting of a metal, an anhydrous metal halide, a Lewis acid, a nitrogen-alkylated lactam or an N,N-disubstituted carboxylic acid amide or phosphoric acid amide at a temperature of about 0° to 170° C.

DESCRIPTION OF THE INVENTION

The present invention now provides a highly efficient process for the preparation of phosphorodichloridodithioates of the general formula

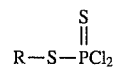

in which

R represents a straight chain or branched alkyl radical with up to 8 carbon atoms (which is optionally substituted by alkoxy or alkylthio), a cycloaliphatic radical with 5 or 6 ring members, an aralkyl radical with 6 to 8 carbon atoms, comprising reacting:

(i) a mercaptan of the general formula R-SH in which R has the above-mentioned meaning, (ii) phosphorous trichloride (PCl₃);

(iii) thiophosphoryl chloride (PSCl₃); and (iv) sulfur;

wherein the reaction is conducted in the presence of a basic catalyst.

The method according to the invention has a number of advantages over the known methods for the preparation of phosphorodichloridodithioates. It requires easily accessible starting materials, which can be reacted in an easily regulated one-pot process to give high yields of the desired products. The process can be used to prepare phosphorodichloridodithioates with a variety of possible substituents. The phosphorodichloridodithioates obtainable in accordance with the process can be isolated from the reaction mixture by simple operations, such as distillation or crystallization. Advantageously, the process does not pollute the environment. The by-product hydrogen chloride can be removed easily and the catalysts can be recycled repeatedly. Hence, it is not necessary to discharge the catalysts from the reaction vessel after they have been used once.

The mercaptan is an alkyl mercaptan selected from the group consisting of methyl mercaptan, ethyl mercaptan, n-propyl mercaptan, isopropyl mercaptan, n-butyl mercaptan, sec-butyl mercaptan, t-butyl mercaptan and isobutyl mercaptan. More preferably, the mercaptan is propyl mercaptan.

In carrying out the process, the reactants are employed in an effective ratio for the production of the phosphoro dichloridodithioate according to the invention. The phosphorus trichloride can be employed in a mole ratio of 0.5 to 1.0 and preferably 0.5 to 0.75 mole per mole of thiophosphoryl chloride. The thiophosphoryl chloride can be employed in a mole ratio of 0.75 to 1.5 and preferably 0.9 to 1.0 mole per mole of mercaptan. It is a distinct feature of the invention that crude thiophosphoryl chloride containing phosphorus trichloride can be used herein as source of the reactants (ii) and (iii) of the claimed invention. Sulfur can be employed in a mole ratio of 1.0 mole per mole of PCl₃.

The catalysts that are useful herein are tertiary amines that can be selected from the group consisting of pyridines such as 5-ethyl-2-methylpyridine, 2-methylpyridine, 2,4-dimethylpyridine, 2,6-dimethylpyridine or 2,4,6-trimethylpyridine; trialkyamines such as tri-n-propylamine and tri-n-butylamine. Preferred herein as the catalyst are 5-ethyl-2-methylpyridine and tri-n-butylamine. The catalyst can be employed in amounts of 0.005 to 0.1 mole of catalyst per mole of mercaptan.

The use of a solvent or diluent when carrying out the process is not necessary, but halogenated hydrocarbons, such as monochlorobenzene or dichlorobenzene, can be employed.

In the following illustrative but non-limiting embodiment of the invention, the process comprises reacting n-propylmercaptan, with crude thiophosphoryl chloride containing phosphorus trichloride in the presence of sulfur. The reaction can be conducted at initial temperatures of about 50° C. to 80° C. and preferably 55° C. to 60° C.

Without being bound to any particular theory, it is believed that the reaction occurs as follows:

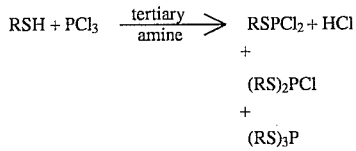

At higher temperatures, all the reagents including $PCl_3$ react with sulfur and this reaction results in the conversion of trivalent phosphorous compounds to pentavalent phosphorus compounds. The higher temperatures can be from 60° to 150° C. and preferably 90° to 140° C. It is believed that this reaction occurs as follows:

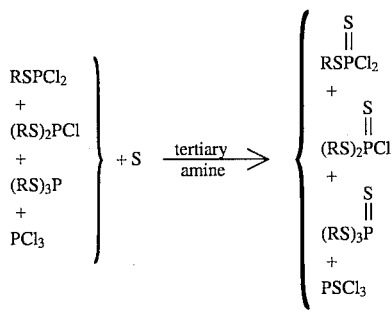

The following equilibration reactions, which also generate phosphorodichloridodithioate, occur at elevated temperatures as well.

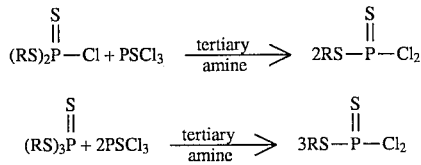

After completion of the reaction and after distilling the excess thiophosphoryl chloride and the phosphorodichloridodithioates, the distillation heel which contains the catalyst, is again reacted with thiophosphoryl chloride and the mercaptan without adding a substantial amount of fresh catalyst. The process for the preparation of the phosphorodichloridodithioates (which are to be purified by distillation) can therefore be carried out by recycling the heel containing catalyst. In general, phosphorodichloridodithioates are liquid and can be separated by distillation under reduced pressure.

As can be seen from the foregoing, the process of the invention can be characterized by the advantage of using a tertiary amine catalyst which produces a fluid heel on distillation of the reaction mixture. The phosphorodichloridodithioates which can be prepared by the process according to the invention may be used as intermediates for the synthesis of insecticidal thiophosphoric acid esters. This novel approach to the preparation of the phosphorodichloridodithioates permits the utilization of crude $PSCl_3$ typically containing 0.5 molar equivalents to 1 molar equivalent $PCl_3$ without sacrificing purity and yield of the phosphorodichloridodithioates.

The invention is further illustrated but is not intended to be limited by the following examples in which all parts and percentages are by weight unless otherwise specified.

EXAMPLES

EXAMPLE 1

Synthesis of n-Propylphosphorodichloridodithioate via the reaction of n-Propylmercaptan with $PSCl_3$, $PCl_3$ and sulfur.
Catalyzed by 5-ethyl-2-methylpyridine

| Charges: | | | |
|---|---|---|---|
| | $PCl_3$ | 68.5 g | (0.5 mol) |
| | Sulfur | 16.0 | (0.5 mol) |
| | $PSCl_3$ | 169.4 | (1.0 mol) |
| | 5-ethyl-2-methylpyridine | 1 g | |
| | n-Propylmercaptan | 76.16 g | (1.0 mol) |

Procedure

To a 1,000 ml 4-necked round bottomed flask, fitted with an overhead stirrer, thermometer, addition funnel, brine cooled condenser (−5° C.), NaOH scrubber system and a nitrogen inlet line, was charged the 169.4 g of $PSCl_3$, 68.5 g of $PCl_3$ and 16 g of sulfur. The resulting mixture was well agitated. To the well agitated mixture was charged a mixture of "heels" (100 g) from previously produced batches of ester dichloride. (The heels were prepared by reaction of $PCl_3$, Sulfur and mercaptan at 90° to 110° C.) This is followed by the addition of 1.0 g of 5-ethyl-2-methylpyridine catalyst to the mixture. The temperature of the mixture was raised gradually to 55° to 60° C. To this reaction mixture was added 76.16g (1.0 mol) of n-propylmercaptan over a period of 1 hour using a gentle nitrogen flow. The reaction temperature was gradually raised to 145° C. and the mixture cooked at this temperature for 4 hours.

The reaction mixture was subjected to vacuum distillation (10 mmHg). A forecut (mostly $PSCl_3$) was collected over a temperature range of 25° to 79° C. A main cut was collected over a temperature range of 95° to 110° C. and it analyzed as 90% ester dichloride. A heel residue comprising

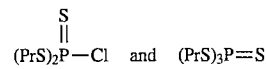

as the main constituents was saved for the next batch. The crude product was further refined via vacuum distillation at 10 mmHg. $PSCl_3$ and dipropyldisulfide (DPDS) were collected as forecuts, the ester dichloride was collected as the main-cut while the higher boiling components were retained in the "heel". The forecuts and the "heel" residues were all combined (approximately 100 g) for recycle to the subsequent batch.

The distilled product analyzed as 97.4% active ingredient (by gas chromatography) and contained 0.4% $PSCl_3$, 0.2% dipropyldisulfide, and 0.5%

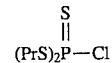

as the main impurities.

This process was repeated over 20 batches using no additional 5-ethyl-2-methylpyridine in subsequent batches. The yield of distilled product, over 20 batches, amounted to 97.0% based on propylmercaptan charged.

EXAMPLES 2–5

In the following examples, there were employed essentially the same procedure and evaluation as described in Example 1. The results are listed in the following tables.

| Catalyst | Run No. | % S‖ RSPCl$_2$ | % DPDS | % Yield on PrSH | Purity |
|---|---|---|---|---|---|
| MEP | 1 | 48.3 | 0.2 | 86.1 | A.I. 97.4% |
| | 2 | 57.2 | 0.3 | 94.1 | |
| | 3 | 62.7 | 0.3 | 96.2 | |
| | 4 | 63.1 | 0.3 | 97.3 | |
| 2,4-Lutidine | 1 | 48.4 | 0.3 | 85.3 | A.I. 97.3% |
| | 2 | 57.0 | 0.3 | 94.7 | |
| | 3 | 62.5 | 0.3 | 96.1 | |
| | 4 | 63.3 | 0.3 | 97.2 | |
| 2,6-Lutidine | 1 | 47.3 | 0.4 | 83.6 | A.I. 97.2% |
| | 2 | 56.8 | 0.3 | 93.9 | |
| | 3 | 62.3 | 0.3 | 97.1 | |
| | 4 | 63.0 | 0.3 | 97.1 | |
| Tributylamine | 1 | 48.5 | 0.2 | 86.2 | A.I. 97.4% |
| | 2 | 57.1 | 0.3 | 94.3 | |
| | 3 | 62.8 | 0.3 | 96.2 | |
| | 4 | 63.5 | 0.3 | 97.5 | |
| N,N-dimethyl-benzylamine | 1 | 47.8 | 0.3 | 85.4 | A.I. 97.2 |
| | 2 | 56.3 | 0.2 | 93.9 | |
| | 3 | 61.8 | 0.3 | 95.8 | |
| | 4 | 62.9 | 0.3 | 96.5 | |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of phosphorodichloridodithioates of the general formula $$\underset{\|}{\overset{S}{R-S-PCl_2}}$$

in which

R represents a straight chain or branched alkyl radical with up to 8 carbon atoms which is optionally substituted by alkoxy or alkylthio, a cycloaliphatic radical with 5 or 6 ring members, an aralkyl radical with 6 to 8 carbon atoms, comprising reacting:

(i) a mercaptan of the general formula R-SH in which R has the above-mentioned meaning;

(ii) phosphorus trichloride;

(iii) thiophosphoryl chloride; and (iv) sulfur wherein the reaction is conducted in the presence of a tertiary amine catalyst.

2. The process of claim 1 wherein the phosphorus trichloride and thiophosphoryl chloride are present in crude thiophosphoryl chloride.

3. The process of claim 1 wherein the amine is selected from the group consisting of 5-ethyl-2-methylpyridine, 2-methylpyridine, 2,4-dimethylpyridine, 2,6-dimethylpyridine, 2,4,6-trimethylpyridine, tri-n-propylamine, and tri-n-butylamine.

4. The process of claim 3 wherein the amine is 5-methyl-2-methylpyridine.

5. The process of claim 3 wherein the amine is tri-n-butylamine.

6. The process of claim 1 wherein the mercaptan is an alkyl mercaptan selected from the group consisting of methyl mercaptan, ethyl mercaptan, n-propyl mercaptan, isopropyl mercaptan, n-butyl mercaptan, sec-butyl mercaptan, t-butyl mercaptan and isobutyl mercaptan.

7. The process of claim 6 wherein the mercaptan is n-propyl mercaptan.

8. The process of claim 1 further comprising distilling the phosphorodichloridodithioate and the by-product thiophosphoryl chloride to provide a fluid distillation heel which retains the catalyst.

9. The process of claim 8 further comprising reacting the distillation heel with a mercaptan, thiophosphoryl chloride and phosphorus trichloride and sulfur without substantial addition of a fresh catalyst.

* * * * *